United States Patent [19]
Watt

[11] Patent Number: 5,685,293
[45] Date of Patent: Nov. 11, 1997

[54] HYPERBARIC FLOW CONTROL SYSTEM

[76] Inventor: Richard W. Watt, 6064 Marylane Ct., Oconomowoc, Wis. 53066

[21] Appl. No.: 602,326

[22] Filed: Feb. 16, 1996

[51] Int. Cl.$^6$ .................. A61M 16/00; A61G 10/00; A62B 31/00; A61H 31/02
[52] U.S. Cl. .................. 128/202.27; 128/202.2; 128/205.26
[58] Field of Search .................. 128/202.12, 200.14, 128/202.27, 204.18, 205.26

[56] References Cited

U.S. PATENT DOCUMENTS

| | | | |
|---|---|---|---|
| 3,367,308 | 2/1968 | Quattrone et al. | 119/420 |
| 3,368,556 | 2/1968 | Jensen et al. | 128/201.21 |
| 3,877,427 | 4/1975 | Alexeev et al. | 128/202.13 |
| 4,195,949 | 4/1980 | Reiher | 405/185 |
| 4,227,524 | 10/1980 | Gelerne | 128/205.26 |
| 4,230,107 | 10/1980 | Butler | 128/205.26 |
| 4,236,513 | 12/1980 | LoPiano | 604/293 |
| 4,448,189 | 5/1984 | Lasley | 600/21 |
| 4,467,798 | 8/1984 | Saxon et al. | 128/205.26 |
| 4,633,859 | 1/1987 | Reneau | 128/205.26 |
| 4,811,729 | 3/1989 | Sands et al. | 128/202.12 |
| 4,893,615 | 1/1990 | Khabirova | 601/16 |
| 5,060,644 | 10/1991 | Loori | 128/202.12 |
| 5,315,990 | 5/1994 | Mondry | 128/205.11 |
| 5,327,904 | 7/1994 | Hannum | 128/205.26 |
| 5,402,775 | 4/1995 | Reneau | 128/202.12 |

*Primary Examiner*—Vincent Millin
*Assistant Examiner*—Eric P. Raciti
*Attorney, Agent, or Firm*—Andrus, Sceales, Starke & Sawall

[57] ABSTRACT

A modular flow control system for a hyperbaric oxygen chamber which receives oxygen gas from a pressurized source and vents a mixture of oxygen and other gases from the chamber to atmosphere. The control system is comprised of a control panel which is mounted to the exterior of the hyperbaric chamber. The control panel consists of an oxygen inlet which is connected to a source of pressurized oxygen and provides access to a system supply line contained within the control panel. The system supply line contains a series of control and gauges which monitor and control the pressure of oxygen within the chamber and the flow rate of oxygen into the chamber. The system supply line terminates at an oxygen outlet which is connected directly to the hyperbaric chamber. Vent gas flows from the hyperbaric chamber back to the control panel through a vent gas inlet. The vent gas inlet is connected to a system vent line. The system vent line contains a series of valves and meters to control the flow of vent gas from the hyperbaric chamber. The system vent line terminates at a vent gas outlet contained in the control panel. A manually operable vent valve is contained in a bypass between the system supply line and the system vent line. The bypass allows the user to vent the supply of pressurized oxygen in a perceived emergency. Each of the connections to the control panel are made by a quick disconnect coupling which allows the control panel to be quickly and easily removed from the hyperbaric chamber.

13 Claims, 2 Drawing Sheets

HYPERBARIC FLOW CONTROL SYSTEM

FIELD OF THE INVENTION

This invention is generally related to control system for a pressure chamber and is specifically directed to a modular flow control system for a hyperbaric oxygen chamber receiving oxygen gas from a pressurized source and venting a mixture of oxygen and other gases to atmosphere.

BACKGROUND OF THE INVENTION

Hyperbaric oxygen therapy (HBO) is a clinically proven technology that has been safely used since the turn of the twentieth century and has become an established treatment procedure for a wide range of human ailments. The following disorders have been shown to respond to hyperbaric oxygen therapy: air or gas embolism, burns, frostbite, carbon monoxide, acute smoke inhalation, crush injury, compartmental syndrome, cyanide poisoning, extensive blood loss, gas gangrene, compromised skin grafts or flaps, and healing wounds.

Hyperbaric oxygen therapy is a medical treatment in which the patient is entirely enclosed in a pressure chamber breathing 100% oxygen at a pressure greater than 1 atmosphere. Breathing 100% oxygen at 1 atmosphere is not considered hyperbaric oxygenation, nor is topical application of oxygen outside a pressurized chamber.

HBO physically dissolves extra oxygen into the blood plasma and tissues. Breathing pure oxygen at 2.5 times normal pressure (2.5 ATA) causes a twelve-fold increase in dissolved oxygen in the plasma compared with breathing at atmospheric pressure. Increased oxygen pressure has been demonstrated to induce formation of new capillaries in ischemic or poorly perfused wounds. Hyperoxygenation is useful in the treatment of ischemic tissue as well as compromised chronic wounds, flaps, and grafts. It is also use in specific infections.

High pressure oxygen causes constriction of the blood vessels in normal tissue without creating hypoxia. However, it does not cause constriction in previously oxygen-deprived tissue. HBO is useful in crush injury and other traumatic ischemic injuries, since it clearly reduces the adherence of white cells to capillary walls, consequently relieving the "no reflow" condition. Reducing of edema is a major benefit of HBO as a result of its preservation of high energy phosphate bonds in the cells. It is also important in preventing progression of deep second degree burns to full thickness injury requiring grafting.

Most of the bodies bacterial defense mechanisms are oxygen dependent. HBO is particularly effective in patients where resistance factors have been compromised, such as dysvascular conditions and immunosuppression disorders. HBO therapy inhibits the growth of a number of anaerobic organisms and enhances the white cell killing of aerobic organisms. The effect of HBO on white cells can double or triple their bacteria-killing ability.

Although the use of HBO therapy has been used for the above-noted human ailments, a new and effective use of HBO has recently been found for treating various illnesses effecting household pets, such as dogs, cats, birds, and other small animals. Since household pets are smaller than human patients, the hyperbaric oxygen chamber which is used to treat the animals can be smaller and more compact than those used for humans. Additionally, since many different species of animals can benefit from the use of the hyperbaric oxygen chamber, the conditions within the chamber must be varied according to the type of animal receiving treatment within.

In many hyperbaric oxygen chambers used for human medical treatment, the control system for the oxygen flow and pressure within the chamber is typically permanently fixed to the outer surface of the hyperbaric chamber. If the control system needs to be adjusted or repaired, a service technician must work on the control system as it is mounted to the hyperbaric chamber, since the physical size of the hyperbaric chamber makes moving the entire chamber to the manufacturer or service department impractical for repairs.

Most current hyperbaric oxygen chambers contain a control system which monitors the pressure of oxygen being supplied to the chamber and controls the amount of gas exiting the chamber. The control systems used in many of the hyperbaric oxygen chambers contain a complex series of measuring devices and control devices to monitor several pressures associated with the hyperbaric chamber. Although these control systems adequately control the pressure within the chamber and the rate of flow of oxygen into and out of the chamber, these systems are often overly complicated and do not provide an efficient method to protect the chamber occupant upon a clinical emergency.

Therefore, it can be appreciated that a hyperbaric oxygen chamber containing a flow control system which is simple in its operation and contains an emergency pressure relief valve would be desirable.

SUMMARY OF THE INVENTION

The invention is related to a modular flow control system that can be used to efficiently and safely control the oxygen gas pressure and flow rate in a hyperbaric oxygen chamber.

The modular flow control system includes a control panel mounted to the exterior of the hyperbaric oxygen chamber. The control panel contains an oxygen inlet connection which is attached to a supply of oxygen gas by a quick disconnect coupling. A system supply line within the control panel connects the oxygen inlet to an oxygen outlet. The oxygen outlet is in turn connected by a hose and a quick disconnect coupling directly to the hyperbaric oxygen chamber.

The modular flow control system further includes a vent gas inlet connection that is directly connected by a quick disconnect coupling and a hose to an outlet port on the hyperbaric chamber. A system vent line within the control panel allows gas entering the control system through the vent gas inlet to flow through the system and exit at a vent gas outlet connection. The vent gas outlet connection is directly coupled to the atmosphere by a hose having a quick disconnect coupling.

A series of oxygen adjusting devices are contained within the system supply line to control the oxygen gas pressure within the chamber and the flow rate of oxygen into the chamber. One of these devices, an adjustable pressure regulator, is positioned adjacent to the oxygen inlet connection to select the oxygen pressure within the chamber. Positioned between the pressure regulator and the oxygen outlet connection is an adjustable flow control valve to control the rate of oxygen entering the hyperbaric chamber.

Contained within the system vent line are a flow meter and a dump rate adjustment device, which are used to control and monitor the flow of gas from the hyperbaric chamber.

A manually operable vent valve is interconnected between the system supply line and the system vent line. The manually operable vent valve is positioned upstream of the adjustable flow control valve in the system supply line and downstream from the vent gas inlet and flowmeter in the system vent line. The manually operable vent valve can be activated to release and quickly vent the oxygen pressure being supplied to the hyperbaric chamber in a perceived clinical emergency.

The modular flow control system can also include a filter in the system vent line upstream of the flow meter to remove any air borne particles before the vent gas reaches the flow meter. Additionally, the control system can include a high pressure relief valve in the system supply line which automatically releases the supplied oxygen if the pressure in the chamber rises above a predetermined level.

In addition, the modular flow control system of the invention is demountably attached to the hyperbaric chamber such that the entire modular control system can be removed and serviced.

Other objects and advantages of the invention will appear in the course of the following description.

BRIEF DESCRIPTION OF THE DRAWINGS

The drawings illustrate the best mode presently contemplated of carrying out the invention.

In the drawings.

DETAILED DESCRIPTION OF THE DRAWINGS

Figure 1:
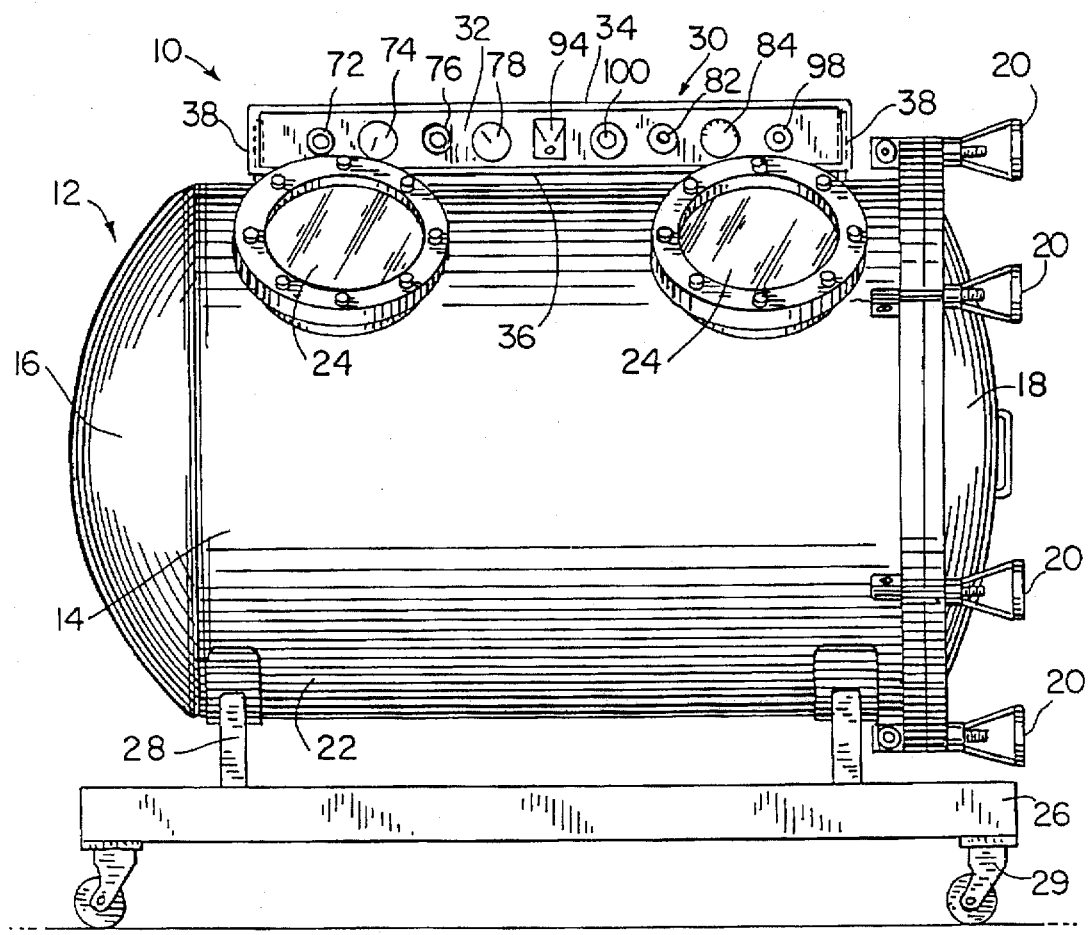
FIG. 1 is a front view of the hyperbaric chamber and control panel in its operative position.

Referring to the drawings, the invention is a modular flow control system 10 for a hyperbaric oxygen chamber, generally designated by the reference 12.

The hyperbaric chamber 12 is a cylindrical pressure chamber adapted to receive oxygen at a pressure greater than one atmosphere. The hyperbaric chamber 12 consists of a body 14, a fixed pressure head 16, and a movable door 18. The door 18 is movable from an open position (not shown) to a closed position shown in FIG. 1. In the closed position, a plurality of hand wheel closures 20 are used to create an air-tight seal between the inner circumferential surface of the door 18 and the end of the body 14.

The body 14 is comprised of a continuous outer wall 22 which defines an open interior portion, not shown. The combination of the outer wall 22, the fixed pressure head 16, and the door 18 in a closed position form an-air-tight open interior into which the patient can be placed for treatment. As can be seen in FIG. 1, in its operative position, the cylindrical axis of the chamber 12 is horizontally disposed. In the preferred embodiment, the door 18 therefore pivots about a vertical axis between its open and closed positions.

A pair of viewing windows 24 are contained in the outer wall 22 which provide an air-tight viewing port into the interior of the hyperbaric chamber 12. These windows 24 allow the physician or veterinarian administering the treatment to monitor the subject contained within the open interior portion of the hyperbaric chamber 12.

The hyperbaric chamber 12 is preferably mounted to a movable cart 26 through a pair of cradles 28. The movable cart 26 allows the physician or veterinarian to position the hyperbaric chamber 12 as desired, through the use of rubber wheeled, 360° swivel casters 29.

The amount of oxygen and the pressure within the hyperbaric chamber 12 are generally controlled by a modular flow control system 10 which is mounted within a control panel housing 30.

Figure 3:
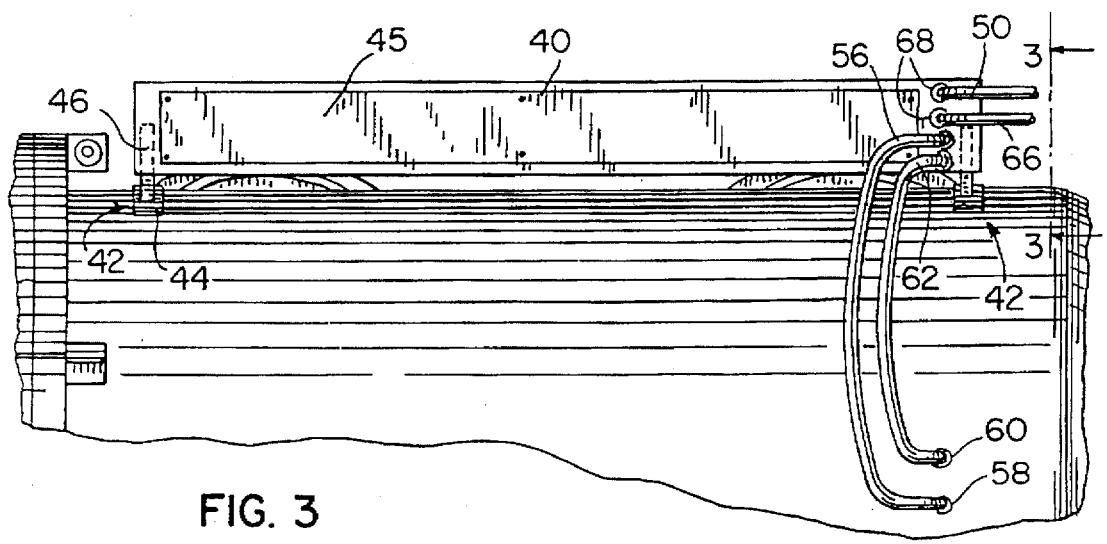
FIG. 3 is a partial back view of the control panel showing the gas line connections.

The control panel housing 30 is generally comprised of a rectangular front face surface 32, a top wall 34, a bottom wall 36, a pair of opposite end walls 38, and a back wall 40 (FIG. 3). In the preferred embodiment of the invention, the housing 30 is constructed of 16-gauge stainless steel. The combination of the face plate 32, the top wall 34, the bottom wall 36, the pair of end walls 38 and the back wall 40 combine to create a control housing 30 which is generally rectangular in shape. As can be seen in FIG. 1, a series of controls and gauges are mounted to the front face plate 32 such that they are clearly visible when the control panel 30 is mounted to the hyperbaric chamber 12. The position and function of the controls and gauges contained on the front face plate 32 will be described in much greater detail.

As can best be seen in FIG. 3, a pair of lifting lugs 42 are securely connected to the outer wall 22 of the hyperbaric chamber 12. The lifting lugs 42 are located at opposite axial ends of the hyperbaric chamber 12 and are generally centered about a vertical axis extending through the center of the chamber 12. The lifting lugs 42 generally consist of a lower cradle 44 and a securely connected vertical lug plate 46, shown in phantom. In the preferred embodiment of the invention, the cradle portion 44 of each lifting lug 42 is fixed to the outer wall 22 of the hyperbaric chamber 12 by welding.

The control housing 30 is sized such that the pair of lifting lugs 42 are both contained within the enclosure defined by the housing 30 when the housing 30 is in its operative position. In particular, the lug plates 46 are located slightly inward from the pair of end walls 38. In this manner, the pair of lifting lugs 42 are effectively concealed when the control panel 30 is in its operative position. The back wall 40 of the control panel housing 30 preferably contains a removable access panel 45 which can be removed to provide access to the controls contained within the housing 30.

Although not shown, the bottom wall 36 of the control panel housing 30 contains a pair of open notches on opposite ends of the bottom wall 36. These open notches receive the pair of lug plates 46, which allows the control housing 30 to be placed in its operative position, as shown.

In the preferred embodiment of the invention, each of the lifting lugs 42 contains an attachment means for securely mounting the control panel housing 30 to the pair of lifting lugs 42. This mounting arrangement between the control panel housing and the lifting lugs 42 is the subject of a co-pending patent application entitled "Control Mounting Apparatus For A Hyperbaric Chamber" by Richard W. Watt, filed on an even date herewith and incorporated by reference herein.

Figure 2:
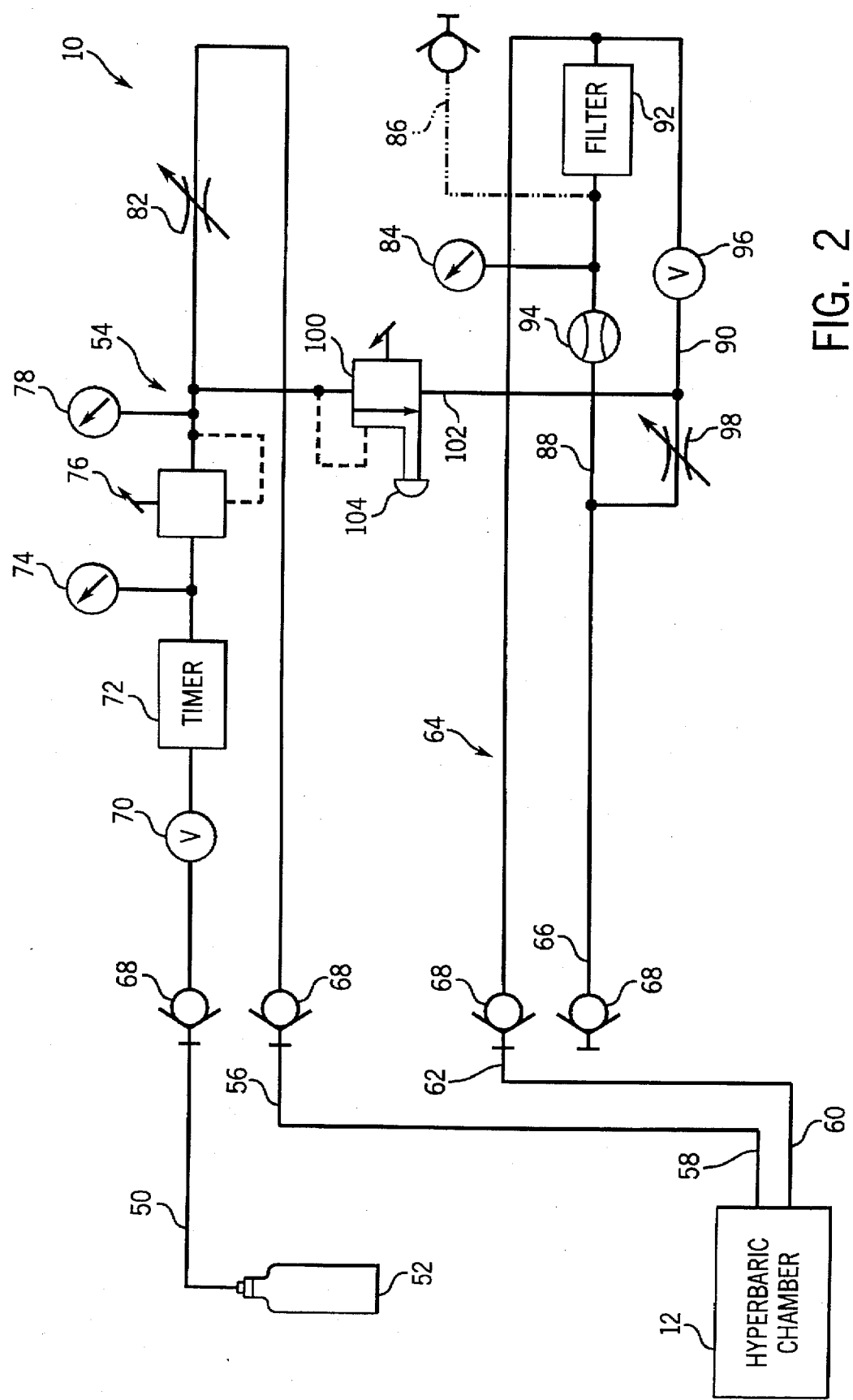
FIG. 2 is a schematic diagram of the flow pattern and control system of the invention.

Referring now to FIG. 2, the detailed flow diagram of the modular flow control system 10 of the invention is thereshown. In the preferred embodiment of the invention, the entire control system shown in FIG. 2 is preferably contained within the control housing 30 and mounted to the hyperbaric chamber 12.

The control system 10 consists of an oxygen inlet connection 50 which is connected to a source of oxygen gas 52. The oxygen inlet connection 50 provides access to the system supply line 54 which is contained within the control housing 30 and terminates at an oxygen outlet connection 56. The oxygen outlet connection 56 is connected directly to an inlet port 58 contained on the hyperbaric chamber 12. In this manner, oxygen from the oxygen source 52 flows into and pressurizes the hyperbaric chamber 12. An outlet port 60 contained in the hyperbaric chamber 12 is directly connected to a vent gas inlet connection 62 contained in the control housing 30.

The vent gas inlet 62 is connected directly to a system vent line 64 which is contained within the control panel housing 30 and terminates at a vent gas outlet connection 66. The vent gas outlet connection 66 is then directly connected to the atmosphere to dissipate the gases leaving the hyperbaric chamber 12.

As can be seen in FIGS. 2 and 3, each of the connections 50, 56, 62, and 66 contains a quick disconnect coupling 68. The quick disconnect couplings 68 allow the various gas line connections to the back of the control housing 30 to be quickly and easily connected or disconnected as needed.

Referring once again to FIG. 2, a series of controls and gauges are contained within both the system supply line 54 and the system vent line 64. An oxygen supply valve 70 is positioned directly downstream from the oxygen inlet 50. The oxygen supply valve 70 is an open/closed valve which allows oxygen to flow through the system supply line 54.

Directly downstream from the oxygen supply valve 70 is a pneumatic timer 72. The pneumatic timer 72 is used to monitor the duration of treatment the patient has undergone within the hyperbaric chamber 12. In the preferred embodiment of the invention, the timer 72 ranges between 0 and 60 minutes. In operation, the pneumatic timer 72 shuts down the flow when it times out and it resets itself after the pressure on it has been removed.

Downstream from the pneumatic timer 72 is an oxygen supply pressure gauge 74 which measures the pressure of the oxygen source 52. In the preferred embodiment of the invention, the oxygen supply pressure gauge 74 measures a range of supply pressure between 0 and 100 psi.

Since the pressure of source 52 is far too high for safe treatment, an adjustable pressure regulator 76 is positioned downstream from the supply pressure gauge 74. The adjustable pressure regulator 76 allows the operator to select the desired amount of pressure within the hyperbaric chamber 12 to be used during the treatment process. Since the hyperbaric chamber 12 can be used for several types of animals, the pressure regulator 76 can be adjusted according to the species being treated. For example, larger dogs require a different pressure setting than a smaller bird or cat.

Directly downstream from the adjustable pressure regulator 76 is a set pressure gauge 78 which indicates the pressure of gas being supplied to the hyperbaric chamber 12. In the preferred embodiment of the invention, the set pressure gauge 78 is calibrated to display a pressure between 0 and 50 psi or 1–3 atmospheres. During normal treatment, the desired pressure within the chamber 12 is typically in the range of 15–30 psi.

Directly downstream from the set pressure gauge 78 in the system supply line 54 is an adjustable flow control valve 82, which is used to set the rate at which the hyperbaric chamber 12 is pressurized. The flow control valve 82 allows the hyperbaric chamber 12 to be pressurized in a range of 1 to 6 psi/minute. Again, the rate at which the hyperbaric chamber 12 is pressurized depends upon the type of patient being treated. The flow control valve 82 can be adjusted by the operator, or in an alternate configuration, preset at a fixed rate which is deemed safe for all patients.

As previously described, the system supply line 54 terminates at an oxygen outlet connection 56. The supply of oxygen then flows into the hyperbaric chamber 12 through the inlet port 58. Oxygen and other gases exhaled by the patient are then vented from the hyperbaric chamber 12 through the outlet port 60. Outlet port 60 is connected to the vent gas inlet 62 contained on the back of the control panel housing 30. The vent gas inlet 62 is connected to the system vent line 64 contained within the control panel housing 30.

Downstream from the vent gas inlet 62 and contained in the system vent line 64 are a pair of branches 88 and 90. Contained in the primary flow path 88 is a filter means 92 which is used to trap airborne particles contained in the system vent line 64. In the preferred embodiment of the invention, the filter means 92 is comprised of a pair of filters which trap particles sized larger than 5 and 500 microns, respectively.

An auxiliary connection 86 is also contained in the system vent line 64. This auxiliary connection 86 can be used to connect a variety of external measuring or monitoring devices to the hyperbaric chamber vent line 64.

Continuing downstream from the filter means 92 is a chamber pressure gauge 84 which indicates the pressure within the hyperbaric chamber 12. By monitoring the chamber pressure gauge 84 and the set pressure gauge 78, the operator can determine if the hyperbaric chamber 12 is correctly sealed. If the two gauges do not correspond to one another after a short period of time required for pressurization, this is an indication that oxygen is escaping the chamber 12 through the door or other opening.

Directly downstream from the chamber pressure gauge 84 is a flow meter 94 which indicates the amount of gas flowing in the system vent line 64. The flow meter 94 measures and controls the flow rate of gas in the range of 1 to 10 cubic feet per minute. Typically, during normal operation of the hyperbaric chamber 12, the flow meter 94 is adjusted to approximately 3 cubic feet per minute. From the flow meter 94, the system vent line 64 continues until it is terminated at the vent gas outlet connection 66.

A depressurization branch 90 is also contained in the system vent line 64. Contained in the depressurization branch 90 is a chamber dump valve 96 which can move between an open and a closed position. When the hyperbaric chamber is being pressurized and used for treatment, the chamber dump valve 96 is closed, which effectively eliminates the depressurization branch 90. However, when the treatment in the hyperbaric chamber 12 is completed, the chamber dump valve 96 is opened which provides a direct path to the atmosphere by bypassing the primary flow path 88 to relieve the pressure within the hyperbaric chamber 12.

To control the rate at which the chamber is depressurized, a chamber dump rate valve 98 is positioned downstream from the chamber dump valve 96. In the preferred embodiment of the invention, the chamber dump rate valve 98 allows the chamber to be depressurized at a rate between 0 and 1 psi per second. The chamber dump rate valve 98 prevents the chamber from being depressurized too quickly.

As earlier stated, the vent gas outlet connection 66 is connected the atmosphere by a quick disconnect coupling 68. This connection to atmosphere can consist of a variety of configurations, none of which are shown in the figures.

Along with the controls previously described, a vent valve 100 is positioned in a bypass connection 102 between the system supply line 54 and the system vent line 64. The bypass connection 102 and vent valve 100 provide a path for the pressurized oxygen supply to vent to the atmosphere without entering the hyperbaric chamber 12. The vent valve 100 contains a push/pull button actuator 104 which can be actuated to open the vent valve 100. The vent valve 100 further contains a high pressure relief valve which is useful as a safety mechanism to vent the supply of oxygen should the pressure within the hyperbaric chamber 12 reach a predetermined unsafe level. The chamber rate valve 98 then controls the rate at which the chamber 12 is depressurized.

In the event of a perceived clinical emergency, the push/pull button actuator 104 can be depressed/pulled by the operator, attending physician or veterinarian. The vent valve 100 then provides a direct path for the pressurized oxygen to atmosphere and effectively bypasses the hyperbaric chamber 12. As shown in FIG. 2, the bypass connection 102 is connected to the depressurization branch 90 downstream from the chamber dump valve 96. Therefore, the bypass 102 provides a direct connection to atmosphere through the chamber dump rate valve 98.

The hyperbaric chamber 12 containing the modular flow control system of the invention is operated as follows. Before commencing operation, the physician, veterinarian, or other operator first checks to see that all vents and vent valves are open and free of debris and that the oxygen supply valve 70 is closed. Next, the operator adjusts the adjustable flow control valve 82 to the required setting to bring the chamber to a desired pressure at a controlled rate. In many applications, the flow control valve 82 will be factory preset at a specific setting.

After setting the flow control valve 82, the physician sets the adjustable pressure regulator 76 to the lowest psi setting. Next, the chamber door is secured through the use of the hand closures 20.

Once these settings are made, the oxygen supply valve 70 is opened and the supply pressure read from the supply pressure gauge 74. The operator then uses the adjustable pressure regulator 76 to adjust the pressure as desired, while reading the set pressure from the set pressure gauge 78. The operator then checks the supply pressure gauge 74, the set pressure gauge 78 and the chamber pressure gauge 84 to assure that the door 18 is properly sealed.

The operator then brings the chamber pressure up to the desired level, while adjusting the flow meter 94 to the desired cubic feet per minute required for the patient contained within the hyperbaric chamber 12. Once the chamber 12 has reached its desired pressure, the operator then sets the timer 70 for the duration of treatment desired.

At the end of the treatment time, the timer 72 times out, cutting off the flow to the chamber 12. The operator then closes the oxygen supply valve 70 to remove the supply of pressurized gas and reset the timer 72. Next, the operator opens the chamber dump valve 96 which allows the hyperbaric chamber 12 to be depressurized at a set rate by the chamber dump rate valve 98. Once the chamber has returned to normal atmospheric pressure, the door 18 is opened and the patient is allowed to exit.

If during the treatment of the patient an emergency situation arises, such as an adverse effect to the pressurized oxygen in the chamber by the patient, the operator can actuate the push/pull button actuator 104 on the vent valve 100. By actuating the actuator 104, the operator creates a direct bypass between the system supply line 54 and the system vent line 64. Therefore, the hyperbaric chamber 12 will be depressurized at a rate controlled by the chamber dump rate valve 98. This vent valve 100 provides an additional safety check in the hyperbaric oxygen control system.

Shown in FIG. 1 are the controls and gauges schematically depicted in FIG. 2 and numbered accordingly. As can be seen in this figure, the controls and gauges are easily accessible and readable by the physician or veterinarian using the hyperbaric chamber 12. Additionally, as previously described, the entire control housing 30 can easily be removed from the hyperbaric chamber 12 to be serviced or adjusted as needed. Removal of the control housing 30 is done by first disconnecting the series of gas line hoses on the back of the control housing 30 via the quick disconnect coupling 68. Once the hoses are removed, the attachment means between the control housing 30 and the lifting lug plates 46 can then be removed. Once the attachment means are removed, the control housing 30 can simply be lifted off of the lifting lugs 42 and transported as desired. In this manner, the modular control system of the invention can be securely attached to the hyperbaric chamber 12 during use and easily removed from the chamber 12, as desired.

It is thought that the present invention and its advantages will be understood from the foregoing description and it will be apparent that various changes may be made thereto without departing from the spirit and scope of the invention and sacrificing all of it material advantages. The form hereinbefore described being merely a preferred embodiment or exemplary embodiment thereof.

I claim:

1. A modular flow control system for a hyperbaric oxygen chamber receiving oxygen gas from a pressurized source and venting a mixture of oxygen and other gases from the chamber to atmosphere, said system comprising:

a control panel mounting an assembly of:

an oxygen inlet connectable to the oxygen source, an oxygen outlet connectable to the chamber, a system supply line interconnecting said oxygen inlet and oxygen outlet, a vent gas inlet connectable to the chamber, a vent gas outlet connectable to atmosphere;

a system vent line interconnecting said vent gas inlet and vent gas outlet, means in said system supply line for adjusting the oxygen gas pressure and flow rate; and a quick disconnect coupling for each of said inlets and outlets.

2. The system as set forth in claim 1 wherein a fastener means dismountably attaches said control panel to the chamber.

3. The system as set forth in claim 1 including a flowmeter in the system vent line.

4. The system as set forth in claim 3 including filter means in said system vent line upstream of said flowmeter and downstream of said vent gas inlet.

5. The system as set forth in claim 1 wherein said oxygen adjusting means comprises:

an adjustable pressure regulator adjacent said oxygen inlet connection; and a first adjustable flow control valve between said pressure regulator and said oxygen outlet connection.

6. The system as set forth in claim 5 including a high pressure relief valve in the system supply line upstream of said pressure regulator.

7. The system as set forth in claim 5 including a manually operable vent valve interconnecting the system supply line upstream of said first flow control valve and the system vent line downstream of said vent gas inlet connection.

8. The system as set forth in claim 7 wherein said vent valve comprises a second adjustable flow control valve.

9. A modular flow control panel for a hyperbaric oxygen chamber receiving oxygen gas from a pressurized source and venting a mixture of oxygen and other gases to the atmosphere, said control panel comprising:

an oxygen inlet connectable to said oxygen source, an oxygen outlet connectable to the chamber said oxygen outlet, a system supply line interconnecting said oxygen inlet and said oxygen outlet;

a vent gas inlet connectable to the chamber, a vent gas outlet connectable to atmosphere, a system vent line interconnecting said vent gas inlet and vent gas outlet, a manually operated vent valve interconnecting said system supply line and said system vent line, means in said system supply line for adjusting the oxygen gas pressure and flow rate, quick disconnect coupling for each of said inlets and outlets; and fastener means for demountably attaching said control panel to the chamber.

10. The system as set forth in claim 9, wherein said oxygen adjusting means comprises:

an adjustable pressure regulator adjacent said oxygen inlet connection;

a first adjustable flow control valve between said pressure regulator and said oxygen outlet connection; and a plurality of pressure indicators for indicating various oxygen pressures in said system supply line.

11. A method of controlling the flow of gas into and out of a hyperbaric oxygen chamber comprising the steps of:

providing a control panel having an oxygen inlet, an oxygen outlet, a vent gas inlet, a vent gas outlet, a system supply line and a system vent line;

connecting a source of oxygen to said oxygen inlet on the control panel with a quick disconnect coupling;

interconnecting said oxygen inlet to said oxygen outlet through said system supply line;

connecting said oxygen outlet to the hyperbaric chamber through a quick disconnect coupling;

connecting the hyperbaric chamber to said vent gas inlet through a quick disconnect coupling;

connecting said vent gas inlet to said vent gas outlet through said system vent line in said control panel;

connecting said vent gas outlet to atmosphere through a quick disconnect coupling;

interconnecting said system supply line to said system vent line through a manually operated vent valve; and demountably attaching said control panel to the hyperbaric chamber.

12. The method of claim 11, further comprising the steps of:

opening an oxygen supply valve;

setting an adjustable flow control valve in said system supply line to control the rate of oxygen flow into the hyperbaric chamber;

setting an adjustable pressure regulator in said system supply line to control the pressure within the hyperbaric chamber;

monitoring the pressure within the hyperbaric chamber; and adjusting the flow of gas leaving the hyperbaric chamber in the system vent line.

13. The method of claim 11, further comprising the steps of:

setting a timer to monitor the amount of treatment given to a patient;

signaling the end of a treatment session; and reducing the pressure within the hyperbaric chamber through a chamber dump valve upon completion of the treatment.

* * * * *